United States Patent [19]

Nazarenko et al.

[11] 4,045,495

[45] Aug. 30, 1977

[54] PROCESS FOR THE PREPARATION OF TRIARYLBORANES

[75] Inventors: Nicholas Nazarenko; William Carl Seidel, both of Orange, Tex.

[73] Assignee: E. I. Du Pont de Nemours and Company, Wilmington, Del.

[21] Appl. No.: 630,995

[22] Filed: Nov. 12, 1975

[51] Int. Cl.² .............................................. C07F 5/04
[52] U.S. Cl. .............................................. 260/606.5 B
[58] Field of Search ................................. 260/606.5 B

[56] References Cited

U.S. PATENT DOCUMENTS

| 2,884,441 | 4/1959 | Groszas | 260/606.5 B X |
| 3,030,406 | 4/1962 | Washburn et al. | 260/606.5 B X |
| 3,090,801 | 5/1963 | Washburn et al. | 260/606.5 B X |
| 3,119,857 | 1/1964 | Yates et al. | 260/462 C |

FOREIGN PATENT DOCUMENTS

| 583,006 | 9/1959 | Canada |
| 814,647 | 6/1959 | United Kingdom |

Primary Examiner—Helen M. S. Sneed

[57] ABSTRACT

Preparation of triarylboranes, e.g. triphenylborane by reacting an alkali metal, e.g. sodium; an organohalide, e.g. chlorobenzene and an orthoborate ester, e.g. triisopropylorthoborate in an inert organic solvent, recovering the borane by contacting the reaction product with water while maintaining the ratio of borane to hydrolysis products (e.g. borinic acid) at at least 13/1, distilling volatiles from the aqueous mixture and contacting the resultant material with acid to a pH not less than about 6 to form the borane.

7 Claims, 1 Drawing Figure

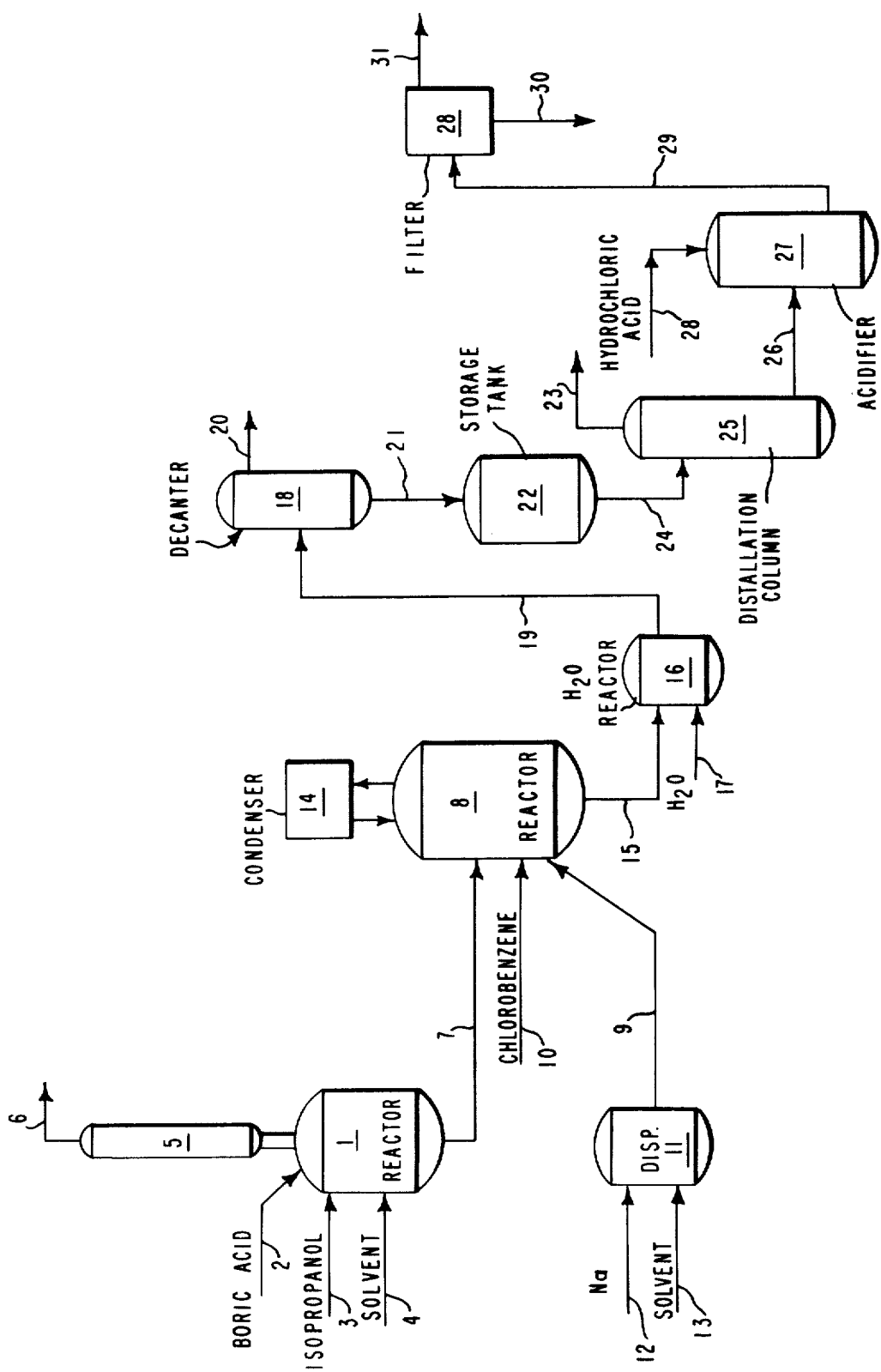

4,045,495

PROCESS FOR THE PREPARATION OF TRIARYLBORANES

BACKGROUND OF THE INVENTION

Field of the Invention

The present invention is directed to an improved process for preparing triarylboranes by reacting an alkali metal, a haloaromatic compound, and an orthoborate ester for the recovery of the borane.

Description of the Prior Art

Organoboranes, i.e. compounds having one or more carbons bonded to boron, have been prepared by a variety of methods including the Grignard reaction using reagents of RmgX type in ether solutions of boron halides. U.S. Pat. No. 2,880,242 discloses an improved process for preparing trisubstituted boranes by the direct action of an organic halide and boron halide in dry ethereal solutions with an alkali metal.

U.S. Pat. No. 3,119,857 discloses the preparation of organoboron compounds by reacting an organo-alkali metal with a boron trihalide or an ester of boric acid in an inert liquid reaction medium to produce the corresponding organoboron halide or organo boric acid ester.

Another process for the preparation of organoboron compounds is disclosed in U.S. Pat. No. 3,187,054 which method involves reacting a boron trihalide, boron ester or boron-carbon compound with an organosodium compound in an inert hydrocarbon solvent. The preparation of a variety of aryl polyboronic acids and esters by reacting an aromatic halide with finely dispersed metallic sodium in the presence of a borate ester preferably at atmospheric pressure and at temperatures below about 50° C. is disclosed in U.S. Pat. No. 3,090,801. The preparation of the sodium hydroxide salt of triphenylborane by reacting triphenylborane with sodium hydroxide is disclosed by Wittig and Raff in an article entitled Über Komplexbildung mit Triphenyl-bor, Ann. 573 208 (1951). The preparation of related compounds, e.g. alkyl phosphines, is disclosed in U.S. Pat. No. 3,223,736.

SUMMARY OF THE INVENTION

The present invention provides a process for the preparation of triarylborane, e.g. triphenylborane by reacting a finely-divided alkali metal, e.g. sodium metal, having a particle size in the range 1–100μ with an organohalide such as a haloaromatic, e.g. chlorobenzene and an orthoborate ester derived from secondary alkyl alcohols, e.g. isopropanol and secbutanol in an inert organic hydrocarbon solvent which can be maintained as a liquid at reaction conditions. Optionally, promoters such as benzene to increase electron transfer and isopropanol to activate the alkali metal may be added. The reaction is conducted in the absence of significant amounts of water, i.e. under substantial anhydrous conditions. The reaction products are contacted with water to form the sodium hydroxide salt of triarylborane. Subsequently the salt is acidified to a pH not less about 6 with an acid, e.g. hydrochloric acid to recover the triarylborane. The alkali metal alkoxide salt of triarylborane can be prepared in one step or in two steps by initially preparing the organosodium compound and subsequently reacting that material with the orthoborate ester. More particularly, one embodiment of the present process involves the preparation of triphenylborane by reacting finely divided sodium, i.e. particles of 1–5μ with chlorobenzene and isopropyl orthoborate using cyclohexane as an inert organic solvent in one or two steps under anhydrous conditions and at a temperature in the range 15°–120° C., contacting the product with water to obtain an aqueous solution of the sodium isopropoxide salt of triphenylborane and acidifying the salt to a pH in the range 7.1–7.4 to obtain the borane while maintaining the ratio of borane to borane hydrolysis products greater than 13/1.

THE DRAWING

A schematic representation of a typical method for practicing the process of the present invention is shown in the drawing.

DETAILED DESCRIPTION OF THE INVENTION

The preferred triarylboranes contemplated by the present invention include those of the formula $R_3$—B wherein R is an aryl or substituted aryl group having 6 to 12 carbon atoms, e.g. phenyl, orthotolyl, paratolyl, naphthyl, methoxy paraphenyl, para-aminophenyl, biphenyl, chlorophenyl and bromophenyl. Triphenylborane and the sodium isopropoxide adduct thereof are of particular interest.

Alkali metals which are operable in the present process include lithium, potassium, etc. with sodium being preferred. The rate and efficiency of the reaction with alkali metal depends at least in part upon the surface area of the alkali metal. Preferably, the metal is in a suspension of particles of 1–5μ in the reaction solvent, but particles up to and exceeding 100μ may be utilized along with certain activators including the lower alkyl alcohols, i.e. those having 1 to 6 carbon atoms, e.g. methanol, ethanol and isopropanol. The activator is preferably employed when the reaction is conducted at lower temperatures and may be introduced directly into the reaction mixture or as a solution in the reaction solvent. If the reaction is conducted at temperatures of 100° C. or higher, e.g. in a methylcyclohexane solvent the sodium can be introduced in the molten state directly to the reaction medium. Since the instant reaction is highly exothermic, the cooling requirements can represent an excessive economic penalty if the reaction is conducted too rapidly. Therefore, it is desirable to control the reaction rate at the desired operating conditions to reduce the cooling requirements. This object can be accomplished without adversely affecting the yield by continuously metering the sodium dispersion to the reaction or by staged addition of the sodium dispersion.

A wide variety of compounds may be employed as the inert organic solvent in the present process. The reactants should be relatively soluble in the solvent at reaction temperature and should not react with the solvent. Compounds such as benzene which increase electron transfer (transfer agents) can be included in the medium especially at lower reaction temperatures. The suitability of certain solvents can vary depending upon the method of conducting the process. For example, in a process wherein the aryllating agent is prepared and then reacted with the orthoester, solvents such as toluene, xylene, and cumene tend to be less desirable because they react with the aryllating agent. However, when the orthoborate ester is present the aryllating agent preferentially reacts with the ester thereby rendering solvents such as toluene essentially inert. Preferably the solvent has a boiling point at atmospheric pressure near the desired reaction temperature to facilitate heat removal via reflux of the solvent. Suitable solvents include singly or in mixture branched or unbranched alkanes, having 5-8 carbon atoms, e.g. pentane, hexane, heptane, octane and 3-methylpentane; cycloalkanes having 5-8 carbon atoms, e.g. cyclohexane, methylcyclohexane, cyclooctane, cyclopentane; alkenes having 5-8 carbon atoms and cycloalkanes having 5-8 carbon atoms wherein unsaturation does not react with the alkali metal, the organohalide or the orthoester. Examples of the foregoing include hexene and octene. Other suitable inert organic solvents will be apparent to one skilled in the art in view of the foregoing consideration. Cyclohexane is preferred because it boils at a preferred reaction temperature and thus permits effective heat removal and because it provides high yield to the desired products when certain esters are employed as is discussed hereinbelow.

The organohalide can be any halogen substituted organic which is compatible in the system and wherein the halogen is available for reaction but any other functional site(s) and substituent group(s) are substantially inert in the reaction. Haloaromatic compounds such as aryl and substituted aryl halides wherein the aryl group has 6-10 carbon atoms are particularly useful. In addition to halogen substituents the aryl halide may be substituted with one or more groups either the same or different selected from the group consisting of alkyl groups having 1-8 carbon atoms, alkenyl groups having 2-8 carbon atoms, aryl groups having 6-10 carbon atoms, alkoxy groups having 1-8 carbon atoms and amino groups having the formula $-NR_2$ wherein R is hydrogen or the above mentioned substituent groups except halogen. It is preferred that the total number of carbon atoms in the aryl halide not exceed 12. Examples of suitable haloaromatic compounds include chlorobenzene, bromobenzene, 4-chlorobiphenyl, 2-chloro-toluene, 4-chlorotoluene, dichlorobenzene, dibromobenzene, octylchlorobenzene, chlorotoluene, parachlorostyrene, octenylchlorobenzene, chlorobiphenyl, naphthylchlorobenzene, parachloroanisole, chlorophenyl octyl ether, parachloroaniline and chloro-N,N'-dimethylaniline. Chlorobenzene is the preferred haloaromatic compound. The amount of organohalide or haloaromatic can vary depending upon its reactivity but preferably should be maintained at a molar ratio in the range 3.5/1-3/1 with respect to the ester in the process where the haloaromatic, alkali metal and ester are reacted simultaneously.

The present invention may be conducted over a wide temperature range, i.e. 15°-120° C. although it is preferred to conduct the reaction at a temperature in the range 40°-65° C. in the case where the alkali metal is reacted with the organohalide before contact with the ester and in the range 75°-105° C. when the reactants are contacted simultaneously.

The borate triesters (orthoborate esters) which are operable in the present invention include those which are derived from an alcohol containing 1-10 carbon atoms and which are represented by the formula $B(OR)_3$ wherein R is selected from the group consisting of methyl, ethyl, n-propyl, isopropyl, n-butyl, sec-butyl, sec-amyl, methylisobutyl, octyl, cyclohexyl, cyclopentyl, phenyl and wherein the R's may be the same or different. Orthoborate esters derived from the lower secondary alkyl alcohols, i.e. those secondary alcohols having 3-8 carbon atoms are especially preferred when cyclohexane is employed as the inert reaction medium because they provide a surprisingly high yield to the desired products when employed in the manner specified herein.

When the process of the present invention is conducted in the preferred manner set forth hereinabove boron containing by-products are less than 6% and preferably less than 3% by weight based upon the weight of triarylborane and the sodium salt adduct of the triarylborane is stable in the aqueous solution.

The present process provides the alkali metal alkoxide salt of triarylborane in sufficient purity so that a subsequent treatment with water yields an aqueous solution wherein the alkali metal hydroxide salt of the triarylborane is stable for extended periods. Although previously disclosed method involved the treatment of reaction products with water, copious amounts of impurities such as borinic acid and precursors present reacted with the minor amount of triarylborane produced when the mixture containing the alkali metal hydroxide salt was acidified resulting in poor recovery of the borane.

Since the salt in the above described aqueous solution is stable, volatile compounds such as alcohols which may be present can be removed from the solution, e.g. by distillation, usually as the water azeotrope or by solvent extraction. Alcohols react with the triarylboranes and especially triphenylborane and therefore represent a yield loss. The distillation is suitable conducted at a temperature in the range 70°-100° C. at atmospheric pressure. Other suitable distillation conditions and suitable solvents should be apparent to those skilled in the art.

After removal of volatile compounds the mixture is acidified with a protonic or Bronsted acid, preferably hydrochloric acid, to a pH not less than about 6 and preferably where the borane is triphenylborane to a pH in the range 6-8 and most preferably 7.1-7.4. It has been discovered that neutralization to a more acidic pH causes rapid acid catalyzed hydrolysis of the triarylborane to form borinic acid. The borinic acid, in turn, accelerates the decomposition. After contact with acid, i.e. upon formation of the triarylborane the product is most sensitive to the aforesaid impurities and to hydrolysis. It is therefore preferred to minimize degradation of the borane by rapidly separating the borane from the aqueous solution preferably as soon as the borane is formed. The ratio of triarylborane to borinic acid in the aqueous solution before acidification should be maintained at greater than 13/1, preferably at greater than 15/1 and most preferably at greater than 20/1 to insure satisfactory yield of triarylborane upon neutralization at least in part to prevent contamination of the triphenylborane with borinic acid as the former precipitates from the aqueous solution. At excessively low ratios it may be necessary to introduce additional water to the system to maintain the borinic acid in solution as the triarylphenylborane is precipitated. It should be apparent from the foregoing that several methods, either singly or in combination, can be employed to insure maximum yield of the triarylborane. It should be noted that the triarylborane is extremely sensitive to oxygen and care should be taken to exclude oxygen during this step of the process.

A more complete understanding of the present invention may be had by referring to the drawing attached hereto and made a part of the specification which describes a specific system for the preparation of boron triphenyl using sodium, chlorobenzene and isopropyl orthoborate in a cyclohexane solvent as the particular reactants. It is understood, however, that the following description is applicable to a wide variety of reactants and solvents as discussed hereinabove.

With reference to the drawing, isopropylorthoborate is prepared in batch reactor 1 by introducing boric acid via line 2, isopropanol in excess of stoichiometric amounts via line 3 and cyclohexane solvent via line 4 into reactor 1 and heating the contents to a temperature of approximately 70° C. Water is produced and continuously removed from reactor 1 by vaporization of a cyclohexane-water isopropanol azeotrope which is directed to overhead condenser 5. The condensate is directed via line 6 to a recovery system which separates the water-isopropanol layer from the organic layer. The organic layer is recycled to reactor 1. Reaction is continued until complete conversion of boric acid is obtained as evidenced by a decrease in the production of water during which time the temperature in the reactor is permitted to rise adiabatically to approximately 80° C. Essentially complete reaction of the boric acid and removal of any excess alcohol is required since unreacted or partially reacted boric acid or alcohol will consume phenyl sodium. The product from reactor 1 is then directed via line 7 to reactor 8 where it is contacted with a sodium dispersion introduced via line 9 and chlorobenzene introduced via line 10. The sodium dispersion is prepared by thorough mixing of molten sodium and hot (100°-110° C.) cyclohexane under pressure in dispersion vessel 11 which is fed by molten sodium stream 12 and cyclohexane solvent stream 13. In the preferred embodiment the sodium dispersion, chlorobenzene and isopropylorthoborate are metered into the reactor in set proportions over about a one-hour period. The reaction is preferably conducted at the boiling point of cyclohexane solvent (about 80° C. at atmospheric pressure) while the heat generated by this highly exothermic reaction is removed by condensing cyclohexane vapor in air condenser 14. After completion of the reaction the reactants are directed via line 15 to reactor 16 where they are contacted with water introduced via line 17 at a temperature of approximately 30°-45° C. to produce the sodium hydroxide salt of triphenylborane and to regenerate isopropanol. Excess sodium will react with water to generate caustic and hydrogen which should be removed and treated by appropriate apparatus not shown. After thorough contact of the reaction mixture with water in reactor 16 the product stream is sent to decanter 18 via line 19 to separate the cyclohexane (oil) phase from the aqueous phase. The oil phase is removed via line 20 and then treated to recover and purify the components for recycle to the process and to remove by-products by suitable apparatus not shown. The aqueous phase is removed from decanter 18 via line 21 to storage tank 22 where the aqueous solution of the sodium adduct of triphenylborane may be retained for extended periods. The triphenylborane is prepared by distilling off alcohol as a water azeotrope (line 23) from the solution in tank 22 (line 24) in distillation column 25. The tails from column 25 are then sent via line 26 to acidifier 27 where the aqueous solution is neutralized by the addition of hydrochloric acid through line 28 at a controlled pH wherein the triphenylborane is precipitated and sodium chloride formed. The aqueous slurry of triphenylborane is directed to filter 28 via line 29 where the aqueous waste containing brine is separated from the borane and discharged for treatment via line 30. Wet triphenylborane is removed via line 31, subsequently washed and dried for final recovery.

The following examples are presented to illustrate but not to restrict the invention. Parts and percentages are by weight unless otherwise indicated. All reagents were at least C.P. grade. Yield is based on ester.

EXAMPLE 1

The apparatus employed consisted of a 500 ml four-necked flask equipped with a mechanical stirrer, thermometer, addition funnel and reflux condenser with suitable provisions to maintain a nitrogen atmosphere over the reactants.

Approximately 40 ml of cyclohexane containing 3.8 grams of sdoium disphersion (particle size 1-5$\mu$) and 2 ml of benzene were charged to the flask and heated to 80° C. A solution containing 9.0 grams of chlorobenzene and 4.7 grams of isopropyl orthoborate in 45 ml of cyclohexane was then added to the flask over a period of 60 minutes while the temperature of the contents were maintained at 80° C. After addition of the chlorobenzene and isopropyl orthoborate the contents of the flask were permitted to cool slowly to room temperature following which 60 ml of water were introduced into the flask. The resultant aqueous and organic phases were removed from the flask and separated. The aqueous phase which contained the sodium salt of triphenylborane was charged to a standard laboratory distillation column where the alcohol was removed by azeotropic distillation at 70°-100° C. over a period of 2 hours. The tails from the distillation wherein the ratio of triphenylborane to borane hydrolysis products was 85/1 were titrated at room temperature with 2.10N hydrochloric acid to a pH of 7.2 whereupon triphenylborane precipitated. The resultant slurry was filtered. The white filter cake was washed with water and vacuum dried to obtain 5.17 grams of triphenylborane (85.4% yield).

Solvent extraction can be substituted for distillation as a method for alcohol removal. A reaction mixture prepared substantially as described in this example was contacted with 75 ml of $H_2O$. The organic and aqueous phases were separated and the aqueous phase which contained the sodium salt of triphenylborane was extracted three times, each time with 40 ml of cyclohexane at room temperature. The aqueous solution was mixed with 150 ml of cyclohexane and then acidified with hydrochloric acid. The cyclohexane layer containing triphenylborane was dried, ammoniated and concentrated under vacuum to yield 78.9% triphenylborane.

EXAMPLE 2

Using the procedure set forth in Example 1, 3.8 grams of finely divided sodium in 40 ml of cyclohexane was added over a 60-minute period to the reaction flask which contained a solution of 5.8 grams of secondary butyl orthoborate and 8.8 grams of chlorobenzene in 45 ml of cyclohexane while maintaining the temperature at 80° C. The product was worked up as set forth in Example 1 to yield an aqueous phase (before distillation) containing 5.8% triphenylborane (89.9% yield) and 0.140% borinic acid (ratio 41/1).

EXAMPLE 3

Using the procedure set forth in Example 1, 3.8 grams of finely divided sodium in 40 ml of cyclohexane was added to a solution of 7.9 grams of methyl isobutyl orthoborate and 9 grams of chlorobenzene in 45 ml of cyclohexane over a one-hour period while maintaining the contents of the flask at 80° C. The product was worked up as set forth in Example 2. Analysis of the aqueous phase indicated a yield of triphenylborane of 74.9%. The estimated ratio of triphenylborane to borane hydrolysis products was 20/1.

EXAMPLE 4

Using the apparatus substantially as described in Example 1 a suspension of 3.8 grams of finely divided sodium dispersion in 40 ml of toluene was charged to the flask and heated to a temperature of 100° C. whereupon the sodium melted. Isopropyl orthoborate (4.7 grams) was then charged to the flask. To the resultant mixture was added dropwise a solution of 9.0 grams of chlorobenzene in 30 ml of toluene over a one-hour period during which time the temperature rapidly rose to and remained at 105° C. Analysis of the aqueous solution obtained as in Example 2 indicated an 88% yield of triphenylborane and a ratio of the borane to hydrolysis products of 33/1.

Substantially the same result was obtained substituting methyl cyclohexane for the toluene and conducting the reaction at 100° C.

EXAMPLE 5

To the apparatus substantially as described in Example 1 was charged 40 ml of toluene and 3.8 g. of freshly cut sodium chunks. The mixture was heated to 105° C. at which point the sodium melted following which 9.0 grams chlorobenzene and 4.7 grams of isopropylorthoborate in 45 ml toluene were added over a one-hour period. After addition was complete, the mixture was stirred for 3 hours at 105° C. The reaction mixture was cooled at room temperature and contacted with water. Analysis of the resultant aqueous layer indicated a 93.2% yield of triphenylborane.

The foregoing example was repeated except that the product was recovered as in Example 1 by neutralization to a pH of 7.2 with a yield of 79.3% at a ratio of triphenylborane to borane hydrolysis products (including borinic acid) of 180/1.

EXAMPLE 6

Four 11.0 gram samples of an aqueous solution of sodium salt of triphenylborane (25.7% weight of borane) were acidified with 2.10N hydrochloric acid to pH's of 8.0, 7.2 and 6.1, respectively and as a comparison to a pH of 1.9. The samples were permitted to stand for about 3 hours following which the sodium salt was formed by the addition of 5% sodium hydroxide and the solutions analyzed in a liquid chromatograph using a mixture of methanol, hexane and ammonia as the mobile phase and a silica gel support. No detectable triphenylborane degradation was observed for the samples acidified to 6.1, 7.2 and 8.0. However the sample acidified to 1.9 showed a decomposition of triphenylborane of 45 weight percent.

EXAMPLE 7

An aqueous solution of the sodium salt of triphenylborane was prepared substantially as set forth in Example 2. The solution was boiled at 100° C. for 90 hours excluding air. No detectable decomposition was observed. This sample failed to indicate any appreciable decomposition after one month of storage.

Examples 1, 5 and 6 describe a preferred method for recovery of the borane. Examples 2, 3, and 4 in addition to Examples 1 and 5 describe the satisfactory preparation of borane having a ratio of borane to hydrolysis products within the above discussed ranges. Example 7 demonstrates the stability of the aqueous solution of the salt of triphenyl borane.

We claim:

1. In a process for the preparation of triarylboranes by reacting an alkali metal, an aryl halide and a borate ester in an inert organic solvent at a ratio of halide to ester in the range of about 3.5:1 to 3:1 and thereafter contacting the reactants with water to obtain an aqueous solution of the alkali metal hydroxide salt of the triarylborane, the improvement which comprises recovering said triarylborane, the improvement which comprises recovering said triarylborane by acidifying said aqueous solution of a pH not less than about 6 to precipitate the borane and thereafter separating the triarylborane from the aqueous solution.

2. The process of claim 1 wherein the triarylborane is triphenylborane and the aqueous solution is acidified to a pH in the range of about 6–8.

3. The process of claim 1 wherein the triarylborane is separated from said aqueous solution at a ratio of triarylborane to borane hydrolysis products of at least 13/1.

4. The process of claim 3 wherein said ratio is at least 20/1.

5. The process of claim 2 wherein the triphenylborane is separated from said aqueous solution at a ratio of triphenylborane to borane hydrolysis products greater than 13/1.

6. The process of claim 5 wherein said ratio is at least 20/1.

7. The process of claim 2 wherein the aqueous solution is acidified to a pH in the range 7.1–7.4.

* * * * *